United States Patent
Nakamura et al.

(10) Patent No.: US 10,392,327 B2
(45) Date of Patent: Aug. 27, 2019

(54) METHYL FLUORIDE PRODUCTION METHOD

(71) Applicant: DAIKIN INDUSTRIES, LTD., Osaka (JP)

(72) Inventors: Shingo Nakamura, Osaka (JP); Yuusuke Etou, Osaka (JP); Keisuke Tano, Osaka (JP); Yoshinori Tanaka, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 15/546,724

(22) PCT Filed: Feb. 5, 2016

(86) PCT No.: PCT/JP2016/053497
§ 371 (c)(1),
(2) Date: Jul. 27, 2017

(87) PCT Pub. No.: WO2016/125891
PCT Pub. Date: Aug. 11, 2016

(65) Prior Publication Data
US 2018/0002257 A1    Jan. 4, 2018

(30) Foreign Application Priority Data
Feb. 5, 2015    (JP) ................. 2015-021408

(51) Int. Cl.
| | | |
|---|---|---|
| *C07C 17/361* | (2006.01) |
| *C07C 19/08* | (2006.01) |
| *C07C 17/383* | (2006.01) |
| *C07C 17/38* | (2006.01) |
| *F25J 3/02* | (2006.01) |

(52) U.S. Cl.
CPC ............ *C07C 17/361* (2013.01); *C07C 17/38* (2013.01); *C07C 17/383* (2013.01); *F25J 3/0219* (2013.01); *F25J 2230/30* (2013.01); *F25J 2290/12* (2013.01)

(58) Field of Classification Search
CPC .................................................... C07C 17/361
See application file for complete search history.

(56) References Cited

U.S. PATENT DOCUMENTS

2015/0299088 A1    10/2015 Nakamura et al.

FOREIGN PATENT DOCUMENTS

| CN | 102762525 A | * 10/2012 | ........... C07C 17/361 |
|---|---|---|---|
| JP | 2005-53901 | 3/2005 | |
| JP | 2012-180285 | 9/2012 | |
| JP | 2014-114277 | 6/2014 | |
| JP | 2015-021408 | 2/2015 | |
| WO | 2005/009933 | 2/2005 | |
| WO | WO-2014077246 A1 | * 5/2014 | ........... C07C 17/361 |

OTHER PUBLICATIONS

Nakamura, S. et al. Publication No. WO2014/077246A1; Published May 22, 2014, pp. 1-8; English translation (Year: 2014).*
Takada, N. et al. Patent No. CN102762525A; Published Oct. 31, 2012, pp. 1-19; English translation (Year: 2012).*
International Search Report dated May 10, 2016 in International (PCT) Application No. PCT/JP2016/053497.

* cited by examiner

*Primary Examiner* — Medhanit W Bahta
(74) *Attorney, Agent, or Firm* — Wenderoth, Lind & Ponack, L.L.P.

(57) ABSTRACT

A method for producing methyl fluoride, comprising the steps of: (1) pyrolyzing a starting compound in a gas phase to thereby obtain a mixed gas containing methyl fluoride and acid fluoride; and (2) rectifying the mixed gas obtained in step (1) to thereby obtain methyl fluoride.

1 Claim, No Drawings

METHYL FLUORIDE PRODUCTION METHOD

TECHNICAL FIELD

The present invention relates to a method for producing methyl fluoride useful as a dry etching gas.

BACKGROUND ART

Hydrofluorocarbons are useful as etching gases for the microfabrication of semiconductors, liquid crystals, and the like. In particular, methyl fluoride ($CH_3F$) is drawing attention as an etching gas for forming state-of-the-art microstructures.

A known method for producing methyl fluoride is, for example, a method in which a mixed gas containing methyl fluoride and acid fluoride is obtained by pyrolyzing a starting compound in a gas phase (PTL 1).

In the above process, as a method for separating methyl fluoride and acid fluoride contained in the obtained mixed gas, PTL 1 proposes a method comprising cooling the mixed gas to separate it into a gas component and a liquid component, the gas component comprising a low-boiling-point component that contains methyl fluoride (boiling point: −79° C.) as a main component, and the liquid component comprising a high-boiling-point component that contains acid fluoride (e.g., 3,3,3-trifluoro-2-(trifluoromethyl)propanoyl fluoride (boiling point: 32° C.) as a main component and may further contain unreacted starting compounds (1,1,3,3,3-pentafluoro-2-trifluoromethylpropyl methyl ether (boiling point: 68.5° C.) etc.).

Further, as another separation method, PTL 1 also proposes a method comprising bringing the obtained mixed gas into contact with water, an aqueous alkaline solution, or the like to dissolve the acid fluoride in an aqueous phase and remove the same. In this case, the use of an alcohol instead of water or an aqueous alkaline solution is also proposed. Bringing the mixed gas into contact with an alcohol to produce an ester makes combustion treatment easier. In a conventional method, the thus-obtained gas containing a large amount of methyl fluoride was further subjected to a rectification operation to purify the methyl fluoride.

CITATION LIST

Patent Literature

PTL 1: JP2014-114277A

SUMMARY OF INVENTION

Technical Problem

An object of the present invention is to provide a method for obtaining a mixed gas containing methyl fluoride and acid fluoride, the method comprising pyrolyzing a starting compound in a gas phase, wherein the methyl fluoride and acid fluoride contained in the mixed gas can be more easily separated.

Solution to Problem

The present inventors conducted extensive research to achieve the above object. As a result, the present inventors found that methyl fluoride can be selectively obtained by directly subjecting a mixed gas to a rectification operation. The present invention has been completed upon further studies based on these findings.

Item 1. A method for producing methyl fluoride, comprising the steps of:
 (1) pyrolyzing a starting compound in a gas phase to thereby obtain a mixed gas containing methyl fluoride and acid fluoride; and
 (2) rectifying the mixed gas obtained in step (1) to thereby obtain methyl fluoride.

Item 2. The method according to Item 1, wherein in step (2), the mixed gas obtained in step (1) is supplied to a rectification column.

Item 3. The method according to Item 2, wherein the supply of the mixed gas is conducted at a pressure exceeding atmospheric pressure, preferably 0.2 MPa to 0.15 MPa.

Item 4. The method according to any one of Items 1 to 3, wherein the starting compound is fluorine-containing methyl ether represented by Formula (1):

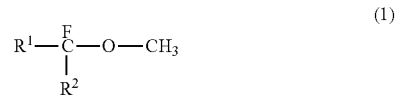

wherein $R^1$ and $R^2$ are the same or different, and each represents optionally substituted linear or branched monovalent aliphatic hydrocarbon, optionally substituted monovalent aromatic hydrocarbon, optionally substituted monovalent cyclic aliphatic hydrocarbon, hydrogen, or halogen.

Advantageous Effects of Invention

According to the present invention, in a method for obtaining a mixed gas containing methyl fluoride and acid fluoride by pyrolyzing a starting compound in a gas phase, the methyl fluoride can be more easily purified from the mixed gas. The details are as follows. Conventionally, it was necessary to remove acid fluoride before purification by cooling the mixed gas and performing fractionation, by washing the mixed gas with water or an aqueous alkaline solution, or by bringing the mixed gas into contact with an alcohol or the like to dissolve the acid fluoride in an aqueous phase and remove the same. In contrast, the present invention does not require such operations before purification. Therefore, the present invention is advantageous in terms of simpler operations. Furthermore, when acid fluoride was removed by bringing the mixed gas into contact with an alcohol, as in conventional methods, components corresponding to industrial waste were inevitably produced due to esterification; however, the present invention does not produce such industrial waste, and is also advantageous in terms of easy handling of the object to be treated.

DESCRIPTION OF EMBODIMENTS

The method of the present invention is a method for producing methyl fluoride, comprising the steps of:
 (1) pyrolyzing a starting compound in a gas phase to thereby obtain a mixed gas containing methyl fluoride and acid fluoride; and
 (2) rectifying the mixed gas obtained in step (1) to thereby obtain methyl fluoride.

1. Starting Compound

The starting compound used in the present invention is not particularly limited as long as it produces a mixed gas containing methyl fluoride and acid fluoride upon pyrolysis in a gas phase.

The reaction that produces a mixed gas containing methyl fluoride and acid fluoride by gas-phase pyrolysis is already known, as disclosed, for example, in JP2014-114277A.

The starting compound used in the present invention is preferably fluorine-containing methyl ether represented by Formula (1):

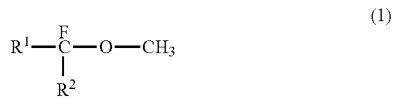

(1)

wherein $R^1$ and $R^2$ are the same or different, and each represents optionally substituted linear or branched monovalent aliphatic hydrocarbon, optionally substituted monovalent aromatic hydrocarbon, optionally substituted monovalent cyclic aliphatic hydrocarbon, hydrogen, or halogen.

There is no particular limitation on the method for producing fluorine-containing methyl ether used as a starting compound, and a compound obtained by any method may be used.

In Formula (1), $R^1$ and $R^2$ are preferably the same or different, and each represents optionally substituted, $C_1$-$C_{30}$ linear or branched monovalent aliphatic hydrocarbon, $C_6$-$C_{12}$ monovalent aromatic hydrocarbon, or $C_6$-$C_{12}$ monovalent cyclic aliphatic hydrocarbon. More preferably, $R^1$ and $R^2$ are the same or different, and each represents optionally substituted, $C_1$-$C_{10}$ linear or branched monovalent aliphatic hydrocarbon, $C_6$-$C_{10}$ monovalent aromatic hydrocarbon, or $C_6$-$C_{10}$ monovalent cyclic aliphatic hydrocarbon.

In the above formula, the $C_1$-$C_{10}$ linear or branched monovalent aliphatic hydrocarbon group is not particularly limited, but is, for example, $C_1$-$C_{10}$ alkyl or the like.

Specific examples of $C_1$-$C_{10}$ alkyl include methyl, ethyl, trimethyl, propyl, 1-methylethyl, hexyl, octyl, and the like. Of $C_1$-$C_{10}$ alkyl groups, $C_1$-$C_6$ alkyl is preferred, $C_1$-$C_4$ alkyl is more preferred, and $C_1$-$C_3$ alkyl is even more preferred.

The $C_6$-$C_{10}$ monovalent aromatic hydrocarbon is not particularly limited, but is, for example, phenyl, methyl phenyl, ethyl phenyl, or the like.

The $C_6$-$C_{10}$ monovalent cyclic aliphatic hydrocarbon is not particularly limited, but is, for example, cyclohexyl, methyl cyclohexyl, ethyl cyclohexyl, or the like.

In the above formula, at least one hydrogen atom of the monovalent aliphatic hydrocarbon, monovalent aromatic hydrocarbon, or monovalent cyclic aliphatic hydrocarbon may be replaced by at least one heteroatom selected from the group consisting of fluorine, chlorine, and bromine; or all hydrogen atoms may be replaced.

In the above formula, the halogen is preferably fluorine, chlorine, or bromine; and more preferably fluorine.

Examples of specific compounds that can be used as starting compounds include, but are not limited thereto, 1,1,3,3,3-pentafluoro-2-trifluoromethylpropyl methyl ether and the like.

In particular, perfluoroisobutylene (($CF_3$)$_2$C=$CF_2$)), which is obtained as a by-product when hexafluoropropene used as a starting compound of fluororesin is produced, has hitherto been discarded as waste; however, 1,1,3,3,3-pentafluoro-2-trifluoromethylpropyl methyl ether can be obtained by reacting perfluoroisobutylene with methanol. Use of the thus-obtained 1,1,3,3,3-pentafluoro-2-trifluoromethylpropyl methyl ether as a starting compound in the present invention allows for effective utilization of waste, and enables the desired product to be produced inexpensively by using the low-cost starting compound. In the present invention, the phrase stating that 1,1,3,3,3-pentafluoro-2-trifluoromethylpropyl methyl ether used as a starting compound is "obtained by reacting perfluoroisobutylene and methanol" is limited to the meaning that the 1,1,3,3,3-pentafluoro-2-trifluoromethylpropyl methyl ether is obtained by said reaction, and is not obtained by other methods. The method for obtaining 1,1,3,3,3-pentafluoro-2-trifluoromethylpropyl methyl ether by reacting perfluoroisobutylene and methanol is a known method, and may be conducted in accordance with known reaction conditions. For example, the reaction may be performed in accordance with the method disclosed in JP2001-506261A.

2. Step (1)

Step (1) of the present invention is to pyrolyze the above starting compound in a gas phase to thereby obtain a mixed gas containing methyl fluoride and acid fluoride.

(i) Catalyst

The catalyst is not particularly limited as long as it is active for a pyrolysis reaction in a gas phase. Examples of such catalysts include metal oxides, fluorinated metal oxides, metal fluorides, and the like. These may be used singly or in a combination of two or more.

Of these, preferable examples of metal oxides include alumina, chromium oxide, titanium oxide, zinc oxide, and the like. In addition, fluorinated metal oxides obtained by fluorinating part of these metal oxides may be used. The fluorinated metal oxide catalysts may be those obtained by fluorinating a metal oxide catalyst with hydrogen fluoride or the like beforehand, or metal oxide catalysts that are partly fluorinated in the reaction process of the production method of the present invention. Preferable examples of metal fluorides include $AlF_3$, $TiF_4$, $CrF_3$, $ZnF_2$, and the like.

Among metal oxides, alumina is preferable, and α-alumina, activated alumina, etc., may be used. Examples of usable activated alumina include ρ-alumina, χ-alumina, κ-alumina, η-alumina, pseudo-γ-alumina, γ-alumina, δ-alumina, θ-alumina, and the like. Of these, γ-alumina and η-alumina are preferable, and γ-alumina is particularly preferable. Silica alumina ($SiO_2$/$Al_2O_3$) a composite oxide, may also be used as a catalyst. The proportion of silica $SiO_2$ in silica alumina is preferably 20 to 90 wt %, and more preferably 50 to 80 wt %.

The larger the pore volume of the catalyst, the higher the activity. The pore volume of the catalyst is preferably 0.4 ml/g or more, and particularly preferably 0.5 ml/g or more. The upper limit of the pore volume of the catalyst is not particularly limited, and is typically 5 ml/g or less, and, in terms of reaction rate and catalyst strength, preferably 2 ml/g or less. The pore volume can be measured by a gas adsorption method, a mercury intrusion method, or the like.

The catalyst may have deposited thereon an alkali metal or alkaline earth metal fluoride, such as KF, NaF, and $MgF_2$.

There is no particular limitation on the method for obtaining the above-mentioned fluorinated metal oxides. For example, the fluorinated metal oxides can be obtained by bringing the above-described metal oxides into contact with anhydrous hydrogen fluoride or a flon while heating to allow a fluorination reaction to proceed. The method for bringing the metal oxides into contact with hydrogen fluoride is not particularly limited, and may be a continuous flow method in which hydrogen fluoride is allowed to flow through a reaction tube containing the catalyst or a batch method in which hydrogen fluoride or a flon is enclosed in a container containing the catalyst. In particular, the flow method is preferable in terms of a short treatment time.

The flon is preferably one with a large number of fluorine atoms and a small number of carbon atoms. Examples of flon include trifluoromethane, difluorochloromethane, octafluoroethane, and the like.

The degree of fluorination of such a metal oxide is not particularly limited; those having a fluorine content of about 5 to about 50 wt % based on the total weight of fluorinated metal oxide are preferably used.

The temperature of the fluorination treatment for such a metal oxide is preferably higher than that of the below-described pyrolysis reaction and is, for example, preferably about 150° C. to about 500° C., more preferably about 200° C. to about 400° C., and even more preferably about 250° C. to about 350° C. An excessively low temperature in the fluorination treatment decreases the effect of the catalyst because of insufficient fluorination, whereas an excessively high temperature in the fluorination treatment additionally requires a heat-resistant material. Thus, an excessively low temperature or an excessively high temperature is not practical.

(ii) Pyrolysis Reaction Conditions

There is no particular limitation on the specific method for allowing a pyrolysis reaction of fluorine-containing methyl ether to proceed by bringing the fluorine-containing methyl ether into contact with the above-described catalyst in a gas phase in the presence of the catalyst. An example is a method in which the catalyst is placed in a tubular flow reactor, and fluorine-containing methyl ether used as a starting compound is introduced to the reactor and brought into contact with the catalyst in a gas phase.

If the temperature of the pyrolysis reaction is excessively low, the conversion of the starting compound tends to decrease. If the temperature of the pyrolysis reaction is excessively high, impurities tend to increase. Thus, the temperature of the pyrolysis reaction is preferably about 100° C. to about 400° C., more preferably about 100° C. to about 300° C., and particularly preferably about 100° C. to about 250° C.

An excessively low pressure in the reactor during the pyrolysis reaction complicates the operation because of the possible contamination of air etc., whereas an excessively high pressure in the reactor during the pyrolysis reaction requires that the pressure resistance of the equipment be considered, and increases the possibility of leakage. Considering these points, the pressure in the reactor during the pyrolysis reaction is preferably about 0.05 to about 1 MPa, more preferably about 0.1 to about 0.5 MPa, and particularly preferably, in terms of reaction operation, about atmospheric pressure (about 0.1 MPa).

There is no particular limitation on the contact time for the reaction. The contact time represented by W/F (g·sec/cc), i.e., the ratio of the amount of the catalyst W (g) relative to the flow rate F (the flow rate at 0° C. and 1 atm (about 0.1 MPa): cc/sec) of the starting material gas, i.e., fluorine-containing methyl ether that is supplied to the reactor, is preferably about 1 to about 100 g·sec/cc, more preferably about 1 to about 50 g·sec/cc, and even more preferably about 5 to about 30 g·sec/cc. If the contact time is too long, it takes a long time to obtain the product. To increase the amount of production, it is preferred that the contact time be shortened; however, if the contact time is too short, the conversion tends to decrease. Thus, the contact time may be selected so that the highest productivity is obtained in terms of the conversion of the starting compound and the selectivity of the desired product, according to the type of catalyst to be used, the amount of the catalyst, the reaction conditions, and the like. In general, it is desirable to conduct the reaction by selecting the contact time so that the conversion becomes 100%, according to the type of catalyst to be used, the amount of the catalyst, the reaction conditions, and the like.

(iii) Mixed Gas

As a result of step (1), a mixed gas containing methyl fluoride and acid fluoride is obtained. The mixed gas contains, in addition the desired product, i.e., methyl fluoride (boiling point: −79° C.), acid fluoride that is simultaneously produced by pyrolysis. The mixed gas may further contain at least one member of starting compounds, by-products, and impurities. Although it varies depending on starting compounds, examples of by-products include propene (boiling point: −47.7° C.), methyl chloride (boiling point: −24° C.), propene pentafluoride (boiling point: −21.1° C.), propane (boiling point: −1.4° C.), and the like.

3. Step (2)

Step (2) of the present invention is to rectify the mixed gas obtained in step (1) to thereby obtain methyl fluoride.

It is therefore not necessary to remove beforehand the acid fluoride before purification by fractionation operations or washing with water or alcohol, and the methyl fluoride can be easily separated from the acid fluoride.

The boiling point of acid fluoride is generally equal to or higher than room temperature; for example, the boiling point of 3,3,3-trifluoro-2-(trifluoromethyl)propanoyl fluoride is 32° C. Thus, the boiling point of acid fluoride is significantly higher than that of methyl fluoride (boiling point: −79° C.). In the mixed gas, methyl fluoride and acid fluoride are present at a molar ratio of 1:1. When the mixed gas is directly placed in an environment at around room temperature, acid fluoride is expected to be condensed. However, the present inventors unexpectedly found a phenomenon in which an interaction occurred between these two components, and the mixed gas as a whole acted as a gas that was not condensed, even at around room temperature (under predetermined pressure conditions). By taking advantage of these findings in the present invention, the mixed gas can be directly subjected to a rectification operation to efficiently separate methyl fluoride.

In step (2), the mixed gas obtained in step (1) is preferably supplied to a rectification column. The supply of the mixed gas is preferably conducted at a pressure exceeding atmospheric pressure. This facilitates the transfer of the mixed gas to the rectification column. The pressure during transfer is more preferably 0.2 MPa to 0.15 MPa. At a pressure within this range, the mixed gas can be effectively supplied to the rectification column, while avoiding the condensation of the mixed gas. As the temperature of the gas after the reaction is higher, the reaction gas can be transferred to the rectification column with a higher pressure. In general, the gas after the reaction is often transferred to the rectification column by a compressor. Moreover, because the pressure of the rectification column is reduced by cooling the temperature of the rectification column, a pressure difference is likely to be formed between the gas inlet side and gas outlet side of the compressor, and the mixed gas can be easily supplied to the rectification column. When the rectification column is cooled, particularly when the vessel of the rectification column in which the solution is stored is cooled, the effect of reducing the pressure of the rectification column increases, and the mixed gas can be more easily supplied to the rectification column.

There is no particular limitation on rectification. In general, two rectification columns are provided, and low-boiling-point components, such as methane or ethylene, are extracted from the top of a first rectification column. The remaining components containing methyl fluoride and acid fluoride are obtained from the bottom of the column, and further supplied to a second rectification column. Then, methyl fluoride can be extracted from the top of the column. In this case, the purity of the methyl fluoride finally obtained from the top of the second rectification column is 99.999 wt. % or more.

EXAMPLES

The present invention is described in more detail below with reference to Examples.

1,1,3,3,3-Pentafluoro-2-trifluoromethylpropyl methyl ether in a gaseous state was flowed into a reactor filled with a γ-alumina catalyst heated to 150° C., and pyrolyzed. The gas after the pyrolysis reaction was collected in a cooled first rectification column while applying a pressure of 0.15 MPa. The composition of the collected reaction gas was as follows.
  Methane: 0.002 mol %
  Ethylene: 0.0036 mol %
  Methyl fluoride: 46.17 mol %
  Propylene: 0.0092 mol %
  1,1,3,3,3-Pentafluoro-2-trifluoromethylpropyl methyl ether: 7.58 mol %
  Acid fluoride: 46.17 mol %
  Other components: 0.0652 mol %

After low-boiling-point compounds, such as methane and ethylene, were removed in the first rectification column, the remaining components were transferred to a second rectification column. After purification in the second rectification column, methyl fluoride was extracted and collected from the top of the rectification column. The purity of the obtained methyl fluoride was 99.999 mol %. Because acid contents such as hydrogen fluoride, and moisture were not produced, a washing column and an alkali column for removing acid contents, a drying column packed with molecular sieves or the like for removing water, etc., were not necessary.

The high-boiling-point components remaining in the rectification vessel of the second rectification column could be introduced unmodified into an incinerator through a stainless steel pipe, and decomposed.

Comparative Example 1

Reaction gas after pyrolysis reaction obtained in the same manner as in the Example was sequentially passed through a washing column, an alkali column containing a 5% potassium hydroxide aqueous solution, and a drying column packed with molecular sieves. Then, the gas was transferred to a first rectification column. After low-boiling-point compounds, such as methane and ethylene, were removed in the first rectification column, the remaining components were transferred to a second rectification column. Purification was performed under reflux in the second rectification column, and methyl fluoride was extracted and collected from the top of the rectification column. The purity of the obtained methyl fluoride was 99.999 mol %.

However, the method of Comparative Example 1 required additional equipment (i.e., the washing column and alkali column), thus increasing the equipment cost. In addition, a mixed solution containing carboxylic acid and hydrofluoric acid produced by hydrolysis of unreacted 1,1,3,3,3-pentafluoro-2-trifluoromethylpropyl methyl ether and acid fluoride was accumulated in the washing column and the alkali column. This waste, which is a mixed solution of an organic substance and a water-soluble substance, causes a problem in that it is difficult to treat the waste as industrial waste. Moreover, because this waste water had high acidity and was capable of corroding metal, the waste could not be directly passed through a metal pipe, such as a stainless steel pipe, and it was difficult to transfer the waste to an incinerator. In order to transfer the waste water, a pipe or container lined with fluororesin etc. was required. Furthermore, extra energy was required to burn the waste water because it contained a large amount of moisture.

Comparative Example 2

Reaction gas after pyrolysis reaction obtained in the same manner as in the Example was sequentially passed through an absorption column containing a methanol aqueous solution, and a drying column packed with molecular sieves. Then, the gas was transferred to a first rectification column. In the first rectification column, low-boiling-point compounds, such as methane and ethylene, were removed. Thereafter, the remaining components were transferred to a second rectification column. Purification was performed under reflux in the second rectification column, and methyl fluoride was extracted and collected from the top of the rectification column. The purity of the obtained methyl fluoride was 99.999 mol %.

However, the use of a large amount of methanol and additional equipment (i.e., the absorption column) were required, thus increasing the chemical cost and equipment cost. In addition, a mixed solution containing ester and hydrogen fluoride produced by reaction of unreacted 1,1,3,3,3-pentafluoro-2-trifluoromethylpropyl methyl ether and acid fluoride with methanol was accumulated in the absorption column. This waste, which was an organic substance but contained hydrogen fluoride, caused a problem in that it was difficult to treat the waste as industrial waste. This waste water did not have high acidity because an organic substance was a main component. However, due to the hydrogen fluoride, which gradually corrodes metal, the waste water could not be passed through a metal pipe, such as a stainless steel pipe, for a long period of time, and it was difficult to transfer the waste water to an incinerator. In order to transfer the waste water, a pipe or container lined with fluororesin etc. was required. Furthermore, extra energy was required to burn the waste water because it contained a large amount of hydrogen fluoride.

The invention claimed is:
1. A method for producing methyl fluoride, comprising the steps of:
  (1) pyrolyzing 1,1,3,3,3-pentafluoro-2-trifluoromethylpropyl methyl ether in a gas phase to thereby obtain a mixed gas containing methyl fluoride and acid fluoride; and
  (2) rectifying the mixed gas obtained in step (1) to thereby obtain methyl fluoride,
  wherein in step (2), the mixed gas obtained in step (1) is supplied to a rectification column, and the supply of the mixed gas is conducted at a pressure exceeding atmospheric pressure.

* * * * *